United States Patent
Saint Felix et al.

(10) Patent No.: US 8,705,817 B2
(45) Date of Patent: Apr. 22, 2014

(54) MEASUREMENT OF GEOMETRIC QUANTITIES INTRINSIC TO AN ANATOMICAL SYSTEM

(75) Inventors: Didier Saint Felix, Verriere le Buisson (FR); Richard Di Monda, Marietta, GA (US)

(73) Assignee: EOS Imaging, Paris (FR)

( * ) Notice: Subject to any disclaimer, the term of this patent is extended or adjusted under 35 U.S.C. 154(b) by 414 days.

(21) Appl. No.: 12/473,258

(22) Filed: May 27, 2009

(65) Prior Publication Data

US 2010/0104150 A1    Apr. 29, 2010

(30) Foreign Application Priority Data

Oct. 24, 2008   (FR) ..................................... 08 57245

(51) Int. Cl.
*G06K 9/00*  (2006.01)
*G06K 9/32*  (2006.01)
*A61B 17/58* (2006.01)

(52) U.S. Cl.
USPC ............ 382/128; 382/154; 382/294; 606/102

(58) Field of Classification Search
None
See application file for complete search history.

(56) References Cited

U.S. PATENT DOCUMENTS

| | | |
|---|---|---|
| 5,699,446 A | 12/1997 | Rougee et al. |
| 2005/0008219 A1 | 1/2005 | Pomero et al. |
| 2005/0149877 A1 | 7/2005 | Rice et al. |
| 2006/0241416 A1* | 10/2006 | Marquart et al. ............. 600/432 |
| 2007/0209220 A1* | 9/2007 | Murphy .......................... 33/512 |
| 2009/0006039 A1* | 1/2009 | Watanabe .......................... 703/1 |
| 2010/0278301 A1* | 11/2010 | Kano .............................. 378/41 |

FOREIGN PATENT DOCUMENTS

| | | |
|---|---|---|
| DE | 102006041055 A1 | 3/2008 |
| EP | 1168249 A1 | 1/2002 |
| EP | 1791087 A1 | 5/2007 |
| FR | 2856170 A1 | 12/2004 |
| WO | 01/37195 A2 | 5/2001 |
| WO | 01/93745 A2 | 12/2001 |
| WO | 02/062249 A1 | 8/2002 |
| WO | 2004/098379 A2 | 11/2004 |
| WO | 2005/030057 A1 | 4/2005 |
| WO | 2008/155772 A1 | 12/2008 |

OTHER PUBLICATIONS

English Abstract of DE102006041055.
English Abstract of EP1168249.
English Abstract of FR2856170.
Search report for FR0857245; Feb. 27, 2009; Clevorn, Jens.

* cited by examiner

*Primary Examiner* — Barry Drennan
*Assistant Examiner* — David F Dunphy
(74) *Attorney, Agent, or Firm* — BCF LLP

(57) ABSTRACT

A method for measuring geometric quantities intrinsic to an anatomical system of a patient, based on two stereoscopic images. Registration data are received on each of the two stereoscopic images. By using geometric calibration information, a three-dimensional geometric primitive is determined defined by at least a portion of the received registration data. Based on the three-dimensional geometric primitive, a value of geometric quantity intrinsic to the anatomical system is computed.

10 Claims, 5 Drawing Sheets

MEASUREMENT OF GEOMETRIC QUANTITIES INTRINSIC TO AN ANATOMICAL SYSTEM

CROSS-REFERENCE TO RELATED APPLICATIONS

The present application claims priority to French Utility Patent Application No. 08 57245 filed Oct. 24, 2008, the entirety of which is incorporated herein by reference.

FIELD OF THE INVENTION

The invention relates to the measurement of geometric quantities intrinsic to an anatomical system.

BACKGROUND OF THE INVENTION

A practitioner, for example a radiologist, a surgeon, or other practitioner, may use geometric quantities, for example a length of a bone, an angle of a scoliosis, or other element, in order to establish a diagnosis.

It is a known practice to take a radiograph of the osteo-articular system of a patient and to measure geometric quantities on the obtained image.

However, the value measured is marred by errors caused by the process of projection of the rays on the plane of the sensor. This error is capable of varying depending on the position of the patient in the frame of reference of the imaging installation.

SUMMARY OF THE INVENTION

The invention remedies this disadvantage by proposing a method for measuring geometric quantities intrinsic to an anatomical system, based on two geometrically calibrated, stereoscopic, two-dimensional images of the anatomical system of a patient, comprising
  (a) receiving registration data comprising at least one set of two-dimensional coordinates, each set of two-dimensional coordinates comprising a first pair of two-dimensional coordinates corresponding to a first point on one of the two stereoscopic images and a second pair of two-dimensional coordinates corresponding to a second point on the other of the two stereoscopic images,
  (b) by using geometric calibration information, determining at least one three-dimensional geometric primitive defined by at least one portion of the registration data received in step (a),
  (c) computing, based on at least one three-dimensional geometric primitive determined in step (b), a value of geometric quantity intrinsic to the anatomical system.

Therefore, the measured geometric quantities are intrinsic to the anatomical system, typically an osteo-articular system. These quantities are therefore independent of the position of the patient in the frame of reference of the imaging installation. If an acquisition of images must be repeated, in order for example to monitor the evolution of a given geometric quantity, the measured geometric quantities are not affected by the variations of position of the patient from one acquisition to the other.

This method is relatively simple for the user and relatively simple to apply.

The stereoscopic images are produced from two different points of view. It is possible to make provision to use a sensor for each point of view in order to acquire the two stereoscopic images simultaneously. As a variant, it is possible to use an arm supporting a source and a detector, capable of rotating about the patient ("C-arm").

The stereoscopic images are in this instance geometrically calibrated, that is to say the two stereoscopic images may be on the same scale or else the two images are each on a particular scale, scale data making it possible to switch from the scale of each of the two images to the scale of the other of the two images.

The scale data may for example comprise, for each of the images, a scale value of the image making it possible to determine a dimension of an object represented on the image from the dimension of the representation of this object on the image. Alternatively, the scale data may simply comprise a ratio between the scale values of each of the images, which may be sufficient to measure geometric quantities of the angle type.

The two stereoscopic two-dimensional images of the said osteo-articular system (or only one of these two images) may be obtained by two respective detectors. They may, for example, be images obtained by X-rays, ultrasound, photographs or other elements.

Alternatively, the two images (or only one of these two images) may be obtained by two respective projections of a three-dimensional model of the osteo-articular system of the patient in distinct directions on virtual planes simulating acquisition planes. The three-dimensional model may, for example, be a model reconstructed, for example, according to the method described in document EP1168249. The images may, for example, be obtained by geometric projections of the contours of the model, which makes it possible to obtain relatively accurate images, or else by simulation of X-rays based on the model, which makes it possible to obtain images resembling radiographs, that is to say a type of image which the practitioner is used to, or else by another projection.

It is possible to find several applications to the measurement of geometric quantities based on two stereoscopic images obtained from a three-dimensional (3D) model. This measurement may for example make it possible to validate the 3D model. Equally, it is possible to choose projection planes such that the practitioner can identify points on the stereoscopic images with relatively high accuracy.

The method described above and below may be applied to the orthopaedic measurement of geometric quantities intrinsic to the osteo-articular system, but equally to the measurement of geometric quantities intrinsic to other body elements, such as the soft tissues that can be seen on the stereoscopic images.

In addition to the sets of two-dimensional coordinates, the registration data may comprise an indication of the geometric quantity which the user intends to measure. It is possible in particular to provide several types of geometric quantities, for example 3-point angle, 4-point angle, distance, or other quantities. A 4-point angle may be defined as an angle between two straight lines of the three-dimensional space each defined by two points of the three-dimensional space.

If, for example, the user chooses to measure a 3-point angle, three sets of two-dimensional coordinates are expected; two three-dimensional geometric primitives, in this instance straight lines intersecting at a point, are determined based on these sets of two-dimensional coordinates, and an angle value between these straight lines is computed.

It is possible to have the registration data include only sets of two-dimensional coordinates, or else only sets of two-dimensional coordinates and an indication of the geometric quantity that the user intends to measure.

It is also possible to have the registration data include primitive-definition data. These primitive-definition data make it possible to define a primitive based on one or more sets of two-dimensional coordinates of the registration data.

For example, the registration data may comprise two sets of coordinates and primitive-definition data comprising a bisecting-plane indication. Therefore, based on these registration data, a segment primitive comprising two points in the 3D space each corresponding to one set of coordinates, and a bisecting-plane primitive of the 3D space containing the bisectors of the segment primitive are defined.

For example, the registration data may comprise four sets of coordinates and primitive-definition data comprising a correction indication so as to define two perpendicular straight lines in at least one of the planes of the stereoscopic images. Two primitives of straight lines each comprising two points in the 3D space respectively defined by corresponding sets of coordinates of the registration data? are initially defined. Secondly, one of these two straight lines, chosen according to the primitive-definition data, is moved so that its projection in at least one of the planes of the stereoscopic images forms a right angle with the projection in this same plane of the other straight line.

As a variant, the registration data may comprise other data, for example distances.

"Geometric calibration information of the stereoscopic images" means information making it possible to deduce a point of view or a sensor-detector distance of one image based on the point of view or the sensor-detector distance of the other image. For example, the geometric calibration information of the stereoscopic images may comprise the absolute positions of the sources and of the detectors for each of the images. As a variant, the geometric calibration information may comprise a relative position of the source relative to the detector for each image. According to another variant, the calibration information may comprise a ratio between the scale values of each of the images, and an oriented angle between the points of view of the images.

A three-dimensional geometric primitive may be described by an analytical expression, that is to say with a limited number of parameters. The primitive determined in step (b) may comprise a sphere, a straight line, a point, a cylinder, a cone, a block, or other element.

The geometric primitive is defined by one portion at least of the registration data received in step (a), without a priori knowledge of the object represented in the images. At least certain parameter values describing the primitive can be deduced from a corresponding portion of the registration data, by using the calibration information. For example, by using geometric calibration information, it is possible to determine a straight line in the three-dimensional space (3D) based on two sets of 2D coordinates received in step (a). This 3D straight line may be described by a straight-line equation with a relatively small number of parameters.

The geometric quantity intrinsic to the osteo-articular system may be computed in the 3D space, for example an angle in the 3D space, for example a cervico-diaphyseal angle, a volume, a distance measured in the 3D space, or other element. As a variant, the geometric quantity may be measured in a plane or on an axis.

The intrinsic geometric quantity may be computed based on one or more primitives. It may for example be the radius of a spherical primitive, or else a distance between a point primitive and a straight-line primitive.

In particular, the geometric quantity may be measured in a plane or an axis of a local coordinate system, attached to the osteo-articular system, and capable of being defined based on registration data received in step (a).

For example, in step (c) it is possible to have at least one geometric quantity value computed in at least one plane, based on at least one projection on this at least one plane of at least one three-dimensional geometric primitive determined in step (b), this at least one plane being defined based on registration data received in step (a). Therefore the geometric quantities, for example an angle, a distance, an area or another quantity, are computed in a plane attached to the osteo-articular system rather than in the plane of one of the detectors.

The plane(s) may be determined by using the calibration information. For example, the user clicks on three points of each of the stereoscopic images and a plane is defined based on the three sets of coordinates thus received.

As a variant, in step (c), at least one geometric quantity value is computed along at least one axis, based on at least one projection on this at least one axis of at least one three-dimensional geometric primitive also determined in step (b). Thus, the measured geometric quantities are one-dimensional, on an axis attached to the osteo-articular system.

These geometric quantities in a plane or on an axis attached to the osteo-articular system of the patient may be more relevant to the practitioner than values measured directly in the 3D space. By using an axis, a plane or a coordinate system attached to the osteo-articular system, it is possible to achieve measurements which are more meaningful to the practitioner.

In addition, the practitioner may be used to measuring certain quantities in a plane, typically the plane of a radiographic image, or on an axis. It may also be more comfortable for the practitioner to access quantities in a plane or on an axis, in particular for the purposes of comparison with geometric quantities measured based on a single radiographic image, according to a method of the prior art.

The geometric quantity may comprise for example an angle in the 3D space, an angle between projections of straight lines of the 3D space on a plane of a local coordinate system, a distance between two points of the 3D space, a distance between a point and a straight line of the 3D space, a distance between two projections of two points of the 3D space on a plane of a local coordinate system, a distance between the projections on a plane of a local coordinate system of a point and a straight line of the 3D space, a volume, an area, or other elements.

Advantageously and in a non-limiting manner, the registration data are received following the selection, by a user, of points on the images with the aid of a user interface. The user therefore appoints points on each of the images, and the geometric quantity value is obtained based on these points, without using a priori knowledge of the imaged object.

Advantageously and in a non-limiting manner, the geometric quantity value computed in step (c) is displayed on a screen, so as to allow the practitioner to continue his analysis. It is possible to make provision, following this display, for the practitioner to enter new registration data, so that the steps (a), (b) and (c), and the display step, are repeated. Such interactivity may be of value for the practitioner, depending on the desired applications.

According to another aspect, a computer program is proposed that comprises instructions for the application of the method explained above, when these instructions are executed by a processor.

According to another aspect, the subject of the invention is a device for measuring geometric quantities intrinsic to an anatomical system, based on two geometrically calibrated, stereoscopic, two-dimensional images of the anatomical system of a patient, comprising (a) means for receiving registration data comprising at least one set of two-dimensional coordinates, each set of two-dimensional coordinates comprising a first pair of two-dimensional coordinates corresponding to a first point on one of the said two stereoscopic images and a second pair of two-dimensional coordinates corresponding to a second point on the other of the said two stereoscopic images, (b) processing means for, by using the geometric calibration information, determining at least one three-dimensional geometric primitive defined by at least one portion of the registration data received by the reception means, and for computing, based on at least one three-dimensional geometric primitive thus determined, a value of geometric quantity intrinsic to the anatomical system.

Such a device, for example a processor, a computer connected to a stereoscopic image acquisition apparatus, or other element, makes it possible to apply the method explained above. The reception means may for example comprise an input port, and the processing means may be incorporated into a processor.

In the present description, an osteo-articular system means both a portion of the complete osteo-articular system of a patient and the complete osteo-articular system.

The patient may be a human or an animal.

BRIEF DESCRIPTION OF THE DRAWINGS

Other particular features and advantages of the present invention will appear in the following detailed description made with reference to the appended drawings in which.

Identical references indicate identical or similar objects from one figure to another.

DETAILED DESCRIPTION

Figure 1:
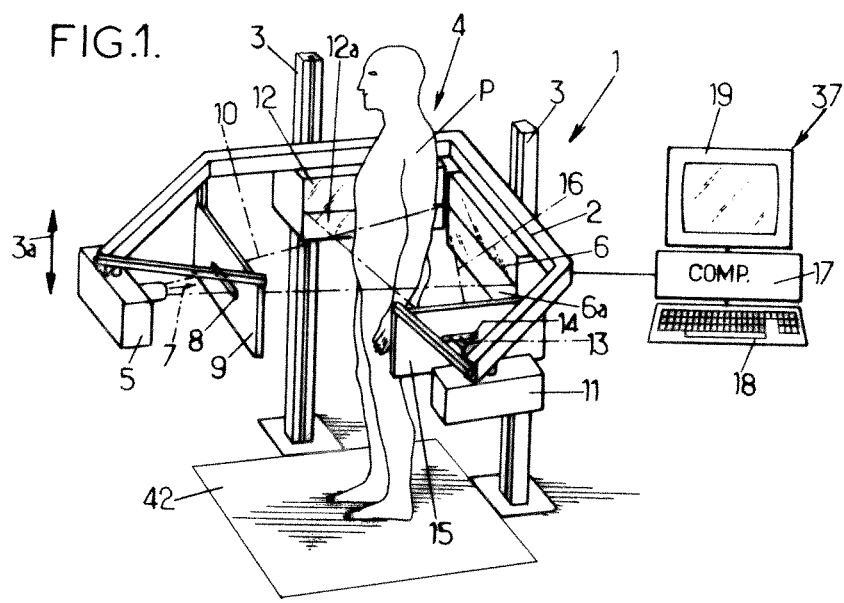
FIG. 1 shows an example of a stereoscopic image acquisition system comprising an example of an orthopaedic measurement device according to one embodiment of the invention.

With reference to FIG. 1, a stereoscopic image acquisition system 1 is shown comprising a support 2 that can be moved along guides 3 in the vertical directions shown by the double arrow 3a.

The support 2 defines a field of observation 4, in which a patient P may be placed, for example standing upright, for the purposes of observation of the osteo-articular system of this patient.

On the support 2 are mounted a first X-ray source 5 and a first detector 6 facing the source 5. This first detector 6 comprises at least one horizontal line 6a of detection cells. For example, the detector 6 may comprise a gas detector, for example like that described in document U.S. Pat. No. 5,959, 302. Naturally, other types of detectors may be used in the context of the present invention.

The source 5 is adapted to transmit ionizing rays, in particular X-rays, capable of being detected by the detector 6, in one shooting direction 7. This direction 7 is substantially from front-to-back or from back-to-front for the patient P.

The rays pass through a slot 8 made in a mask 9, for example a metal plate, so as to generate a horizontal beam 10 of ionizing rays in the field of observation 4.

A second source 11 similar to the source 5 is also mounted on the support 2. A second detector 12 similar to the detector 6 is mounted on the support 2 so as to face the source 11. This detector 12 comprises at least one horizontal line 12a of detection cells.

The source 11 is adapted to transmit ionizing rays in a shooting direction 13 which is substantially sideways relative to the patient P. The rays transmitted by the source 11 pass through a horizontal slot 14 formed in a mask 15, for example a metal plate, so that a horizontal beam 16 of X-rays is generated in the field of observation 4.

Naturally, it is possible to provide more than two sources and more than two detectors. In addition, the shooting directions 7 and 13 do not have to be substantially perpendicular to one another. For example, it is possible to provide an angle of 30° between these shooting directions. Moreover, the plane defined by the shooting directions 7, 13 do not have to be parallel, or even substantially parallel, to the plane of the ground. The shooting directions 7 and 13 may therefore be any direction, provided that they effectively make it possible to obtain two images of the osteo-articular system of the patient and provided that they are not colinear with one another.

The detectors 6, 12 are connected to an information technology system 37, or else to any other electronic control system fitted:

with a user interface comprising an input interface comprising a keyboard 18, and usually also a mouse (not shown), and an output interface comprising at least one screen 19;

an orthopaedic measurement device, for example a processor 17 capable of executing the instructions of a computer program.

In this embodiment, a device for reconstructing a 3D model from two stereoscopic images is supplied. This device is for example incorporated into the processor 17. The processor 17 may comprise or be connected to a memory not shown storing at least one a priori model of the structure to be reconstructed. This a priori model is established from an a priori knowledge of the structure to be reconstructed.

The computer 37 may be connected to motorized means contained in the guide 3, and to the sources 5, 11, so as to control the vertical movement of the support 2 and the transmission of the X-rays.

During an acquisition of a pair of stereoscopic images, the support 2 is moved vertically, so as to cover a relatively extensive portion of the osteo-articular system.

Such a system 1 therefore makes it possible to obtain two stereoscopic images, acquired simultaneously, of the osteo-articular system of the patient. The position of the patient relative to the frame of reference (or "coordinate system") of the imaging installation determines the point of view of the representation of the osteo-articular system on each of these images.

Figure 2:
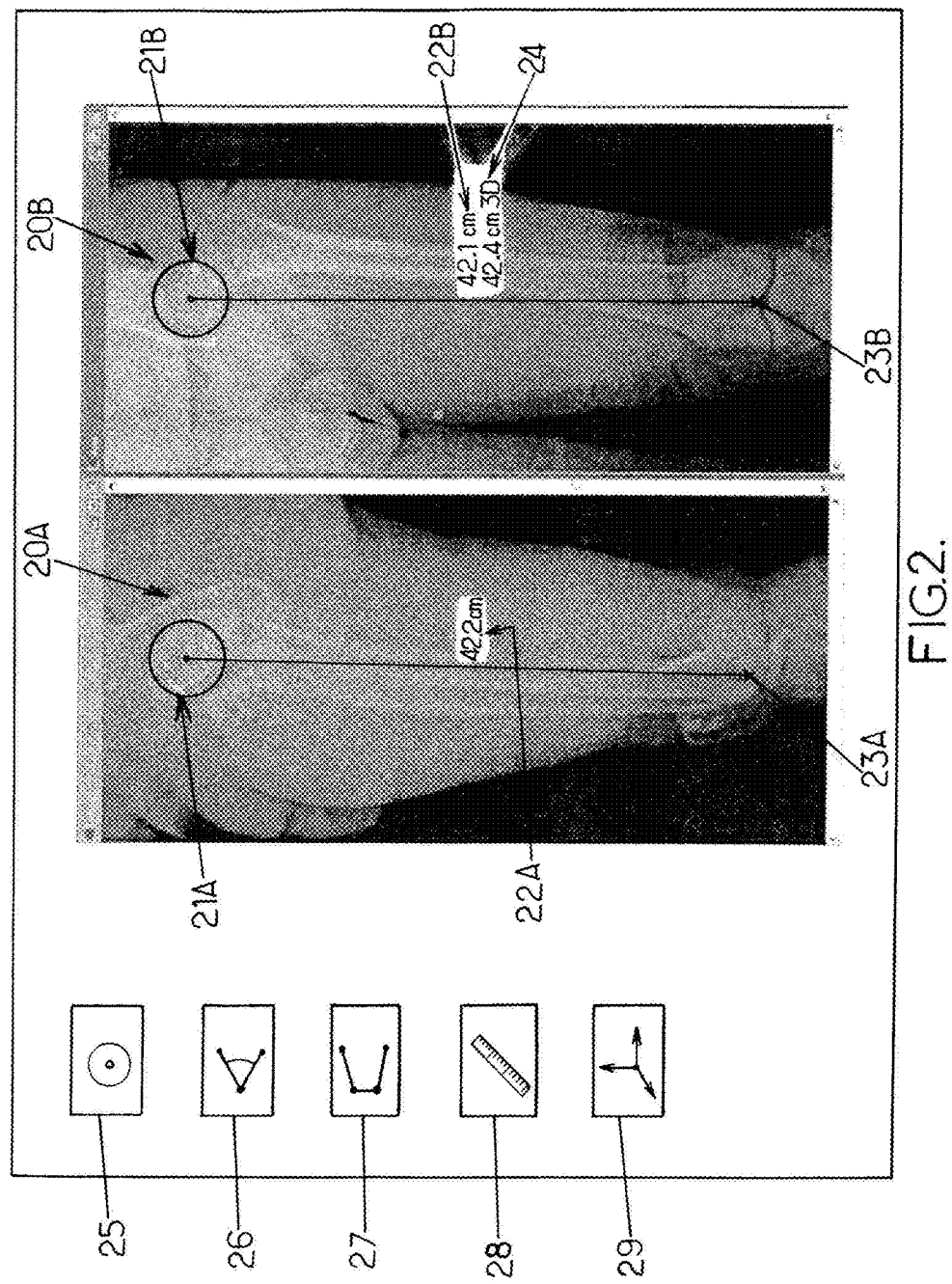
FIG. 2 shows an example of a graphic interface that can be displayed by an example of an orthopaedic measurement device according to one embodiment of the invention.
Figure 3:
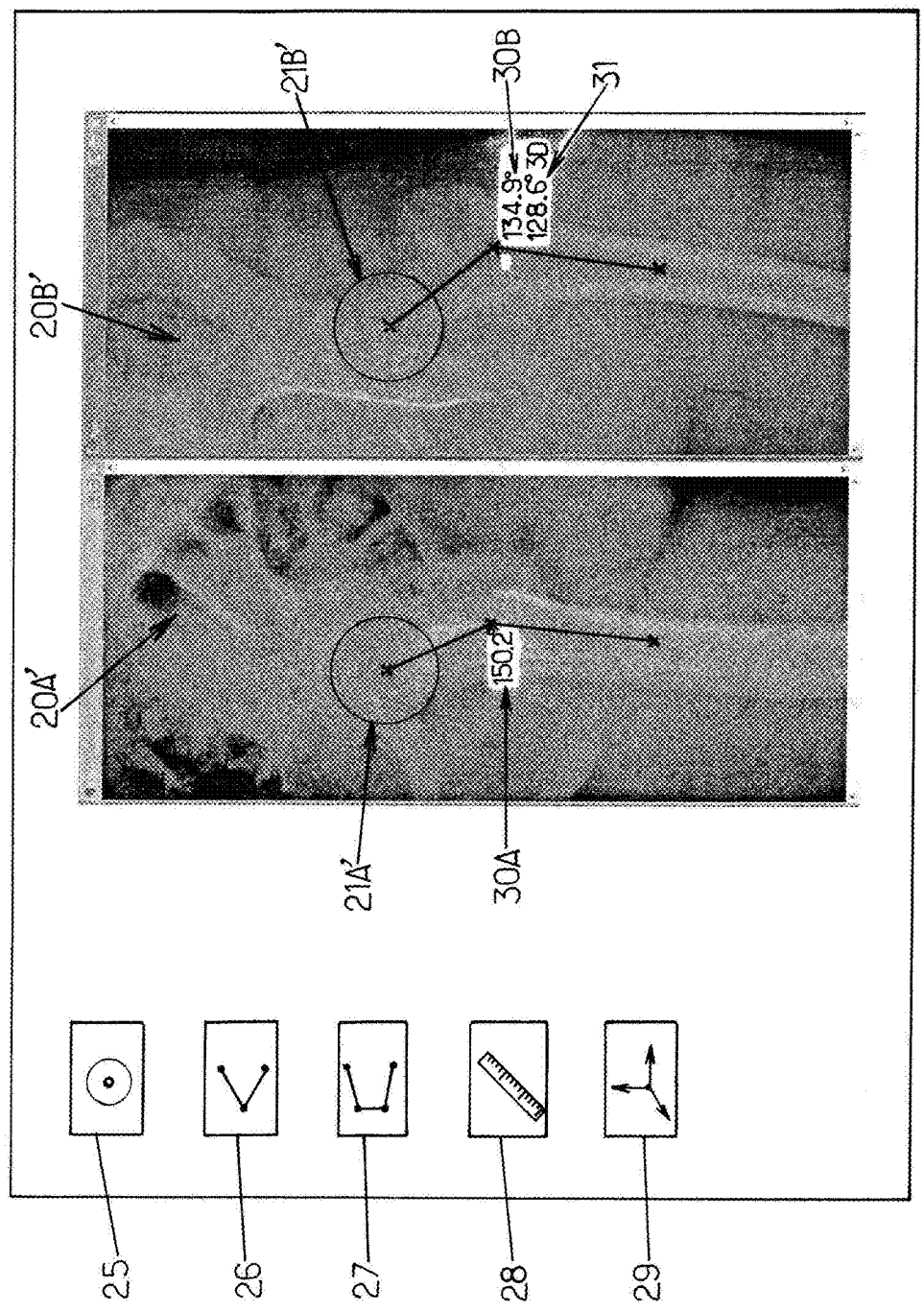
FIG. 3 shows an example of a graphic interface that can be displayed by an example of an orthopaedic measurement device according to one embodiment of the invention.

FIGS. 2 and 3 show an example of a graphic interface that can be displayed on the screen 19 of the computer 37, or else on another screen. In these two figures, the graphic interface is identical; only the stereoscopic images displayed and the quantities measured vary.

This graphic interface makes it possible to display the stereoscopic images 20A, 20B, 20A', 20B'.

Also appearing are icons 25, 26, 27, 28, 29. Each of the icons 25, 26, 27, 28 corresponds to one type of geometric quantity, for example 3-point angle, 4-point angle, distance. The icon 25 may correspond to a quantity of radius or diameter of a sphere.

Figure 4:
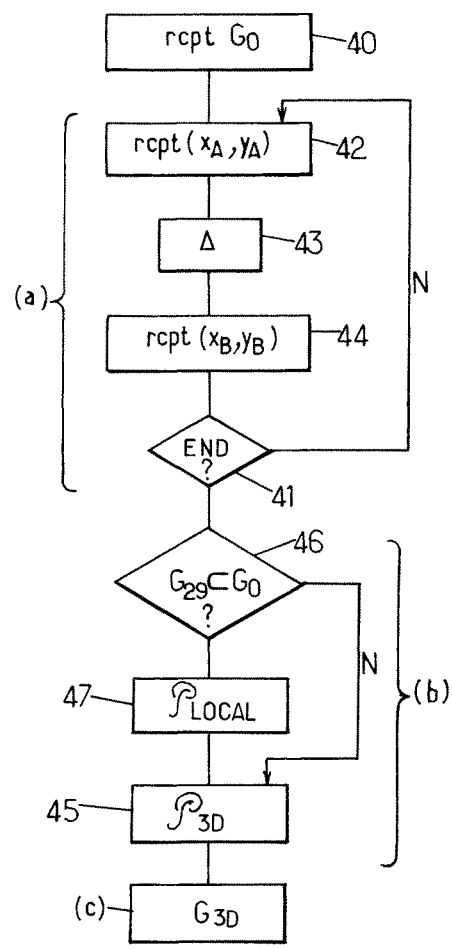
FIG. 4 shows an example of an algorithm of a method according to one embodiment of the invention.

FIG. 4 shows an example of an algorithm of orthopaedic measurement of geometric quantities intrinsic to an osteo-articular system, based on two geometrically calibrated stereoscopic views of this osteo-articular system. These two images may be obtained by using the system of FIG. 1, and be displayed on the graphic interface of FIGS. 2 and 3. FIGS. 2, 3 and 4 will be commented on simultaneously.

The user may begin by clicking on one of the icons 25 to 29 so that the processor (reference number 17 in FIG. 1) receives, during a step 40, an item of information relating to the type of geometric quantity that the user desires to measure.

The user then selects certain points on the images 20A, 20B, 20A', 20B'. The device thus receives, during a step (a), registration data comprising sets of two-dimensional coordinates, each set of two-dimensional coordinates comprising two pairs of two-dimensional coordinates corresponding to two points on respectively one and the other of the stereoscopic images.

The number of sets of coordinates received varies depending on the selected icon. The end-of-acquisition test 41 therefore varies depending on the information received in step 40.

For example, if the user selects the icon 26 corresponding to a 3-point angle quantity, this acquisition step (a) ends when the three sets of coordinates are received. The test 41 therefore consists in comparing the number of sets of coordinates received with a threshold.

For example, if the user has selected the icon 27 corresponding to a 4-point angle quantity, this acquisition step (a) ends when four sets of coordinates are received.

For example, if the user has selected the icon 28 corresponding to a distance quantity, this acquisition step (a) is brought to an end when two sets of coordinates are received.

For example, if the user has selected the icon 25 corresponding to a quantity relating to a sphere, the user may, in order to position two circles corresponding to the sphere respectively on the two images, on the one hand move these circles, and on the other hand stretch these circles. The device is therefore capable of receiving a number of sets of coordinates which does not have to be predefined. It is possible to provide that the user clicks on an icon not shown, or on another portion of the graphic interface, in order to confirm the positions of the circles. The test 41 may then consist in detecting this click.

Advantageously, for each set of coordinates received, each pair of coordinates is in a locus of potential of the corresponding image, this locus of potential being able to be determined based on the other pair of coordinates and on geometric calibration information between the images. In other words, because of the relative positions of the sources (reference numbers 5, 11 in FIG. 1, or $S_A$, $S_B$ in FIG. 5) and of the detectors (reference numbers 6, 12 in FIG. 1, or $D_A$, $D_B$ in FIG. 5), the user chooses sets of coordinates defining points of the 3D space.

In particular, it is possible for example to provide a step 42 for receiving a first pair of coordinates $x_A$, $y_A$ that is to say that the user begins by selecting a point on one 20A of the images, called the first image.

Figure 5:
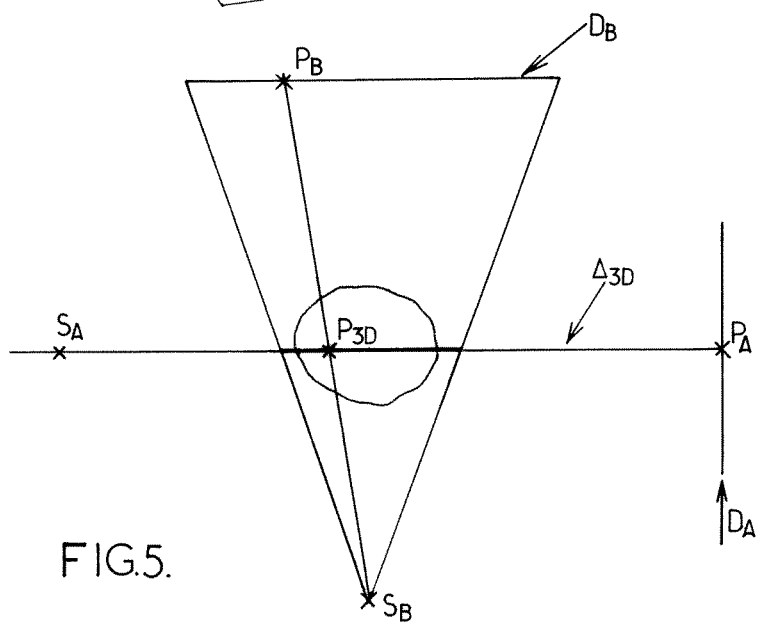
FIG. 5 illustrates a step for determining a locus of potential for a method according to one embodiment of the invention.

During a step 43, a locus of potential $\Delta$ is determined on the other image 20B, called the second image. FIG. 5 illustrates this determination of the locus of potential. A straight line $\Delta_{3D}$ is defined in the 3D space between a point $P_A$ on the detector $D_A$ corresponding to the coordinates $x_A$, $y_A$ on the first image and a point $S_A$ of the 3D space corresponding to the source. Then an imaging with the other source (corresponding to the point $S_B$) and the other detector (corresponding to the point $D_B$) of this straight line $\Delta_{3D}$ is simulated. The locus of potential $\Delta$ therefore corresponds to the simulated image of this straight line $\Delta_{3D}$ on the other image 20B. Each point in this locus of potential $\Delta$ of the image 20B defines with the point corresponding to the coordinates $x_A$, $y_A$ on the image 20A a point of the 3D space.

This locus of potential $\Delta$ is displayed on the second image 20B.

The user then clicks on a point of this locus of potential on the second image 20B, so that the device receives, during a step 44, a second pair of coordinates $x_B$, $y_B$.

The steps 42, 43, 44 represent a relatively simple registration data acquisition algorithm. It is possible to provide additional steps not shown in order to give the user more freedom for fixing the sets of coordinates. For example, it would be possible to allow the user the choice of clicking on the second image in a location other than on the locus of potential defined in step 43. A locus of potential would then be determined on the first image, defined by the new point clicked. The set of coordinates could therefore be defined by successive selections.

Naturally, it would be possible to make provision not to display a locus of potential, but a single point of this locus of potential, which the user would move as he wishes on the graphic interface.

Alternatively, it is possible to make provision to allow the user to choose two points on the images 20A, 20B, without imposing any constraint, then, by using the calibration information, to determine from the coordinates of these two entered points a set of coordinates that would correspond to a point of the 3D space and that would be relatively close to the set of coordinates entered by the practitioner.

The invention is therefore in no way limited by the manner in which this step (a) is operated.

There follows a step (b) during which, by using geometric calibration information, at least one three-dimensional geometric primitive is determined, defined by at least one portion of the registration data received in step (a).

This determination may be based on the same geometric principles as the determination of a locus of potential. Specifically, each pair of coordinates obtained corresponds to a pair of points $P_A$, $P_B$ in FIG. 6, and to a point $P_{3D}$ of the 3D space. This point of the 3D space may be determined relatively easily, by using for example the relative positions of the sources and of the detectors. And once the point(s) of the 3D space is (are) determined, it is relatively easy for those skilled in the art to obtain geometric primitives of the straight line, sphere or other type.

For example, if the user has chosen to measure a 3-point angle, the three sets of coordinates received in step (a) make it possible to define, by using the calibration information, three points of the 3D space. These three points of the 3D space make it possible to define two straight lines intersecting at a point (step 45).

For example, if the user has chosen to measure a 4-point angle, the four sets of coordinates received in step (a) make it possible to define two straight lines of the 3D space during step 45.

For example, if the user has chosen to measure a distance, the two sets of coordinates received in step (a) make it possible to define two points of the 3D space, or a straight-line segment of the 3D space during step 45.

For example, if the user has clicked on the "sphere" icon, the sets of coordinates received make it possible to define a sphere of the 3D space during step 45.

Finally, during a step (c), based on at least one three-dimensional geometric primitive determined in step (b), a geometric quantity value intrinsic to the osteo-articular system of the two stereoscopic images is computed.

For example, if the user has chosen to measure a 3-point angle or a 4-point angle, based on the two straight lines defined during step 45, an angle between these two straight lines is computed.

For example, if the user has chosen to measure a distance, the distance in the 3D space between the two points of the 3D space determined during step 45 is computed.

If the user has clicked on the "sphere" icon, based on the sphere defined in step 45, a radius of the sphere for example is determined.

With reference to FIG. 2, the user has clicked on the icon 25 and adjusted two circles 21A, 21B on the two images 20A, 20B, in order substantially to coincide with the representations of the condyles in these images. During step (b), a sphere is defined in the 3D space based on these adjusted circles 21A, 21B.

The radius of the sphere may be determined during step (c) and may supply information concerning the size of the condyle of the patient, for example for prosthesis-manufacture applications.

The sphere defined in step (b) may be used to determine the position in the 3D space of its centre. Specifically, it may be awkward for the practitioner to identify the centre of a condyle by simply pointing to points. By using a sphere primitive, the practitioner uses the representations of the edges of the condyles on the images to determine this centre.

The position in the 3D space of this centre, obtained following step (b) for defining the sphere primitive, may itself be used to define other geometric primitives.

For example, in FIG. 2, the aim is to measure a distance in the 3D space between the centre of the condyle and the other end of the femur. A point of the 3D space corresponding to this other end is defined in step (b), based on a set of coordinates received in step (a) corresponding to the points 23A, 23B.

During the step (c), a distance in the 3D space between these two points of the 3D space is computed.

In the example shown, a distance in the 3D space of 42.4 cm (reference 24) is obtained. The distances 22A, 22B measured directly in the planes of the images, between the centres of the circles 20A, 20B and the points 23A, 23B respectively, are 42.2 cm and 42.1 cm.

In the example of FIG. 3, the practitioner has also used a sphere primitive in order to determine a point of the 3D space corresponding to the centre of a condyle. Two other points of the 3D space are defined based on two sets of coordinates received in step (a). During step (c), an angle in the 3D space is computed based on the positions in the 3D space of these three points.

In the example shown, an angle in the 3D space of 128.6° is obtained, while the angles measured in the planes of the images are 150.2° for the image 20A' and 134.9° for the image 20B'.

The graphic interface of FIGS. 2 and 3 comprises an icon 29, called the local coordinate system icon. This icon makes it possible to define a local coordinate system, based on sets of coordinates entered by the practitioner.

When the practitioner clicks on this icon, he manipulates representations in two dimensions of a three-dimensional coordinate system, in the same way that he manipulates circles when he clicks on the icon 25. The practitioner may therefore position and orient these representations of the local coordinate system, so that, during the step (b), a local coordinate system can be defined in the 3D space, based on the geometric calibration information and based on sets of coordinates entered by the practitioner during the positionings/orientations.

This local coordinate system defined in the 3D space makes it possible to define in particular at least one plane of the 3D space, for example the plane XY of the local coordinate system and/or the plane XZ.

For example, the step (b) comprises a test step 46: if some of the registration data received in step (a) correspond to a 3D coordinate system, a local coordinate system is defined during a step 47.

It can be envisaged, during the step (c) of computing a geometric quantity, to project some or all of the primitives obtained in step (b) other than this 3D coordinate system in one or more planes of the 3D coordinate system.

For example, the straight lines defined in the 3D space during step (b) are projected in one of the planes also defined in step (b).

One or more of the geometric quantity values are then computed based on this or these projections in one or more planes of the local coordinate system.

For example, an angle is computed in the plane of the local coordinate system between the projections in this plane of two straight lines defined in step (b).

For example, a distance is computed in the plane of the local coordinate system between the projections in this plane of two points of the 3D space, or else between the orthogonal projections in this plane of a point of the 3D space and of a straight line of the 3D space.

As a variant, the local coordinate system defined in the 3D space makes it possible to define in particular at least one axis of the 3D space, for example the axis X of the local coordinate system, the axis Y and/or the axis Z. It can be envisaged, during step (c) of computing a geometric quantity, to project some or all of the primitives obtained in step (b) other than this 3D coordinate system in one or more axes of the 3D coordinate system.

Figure 6:
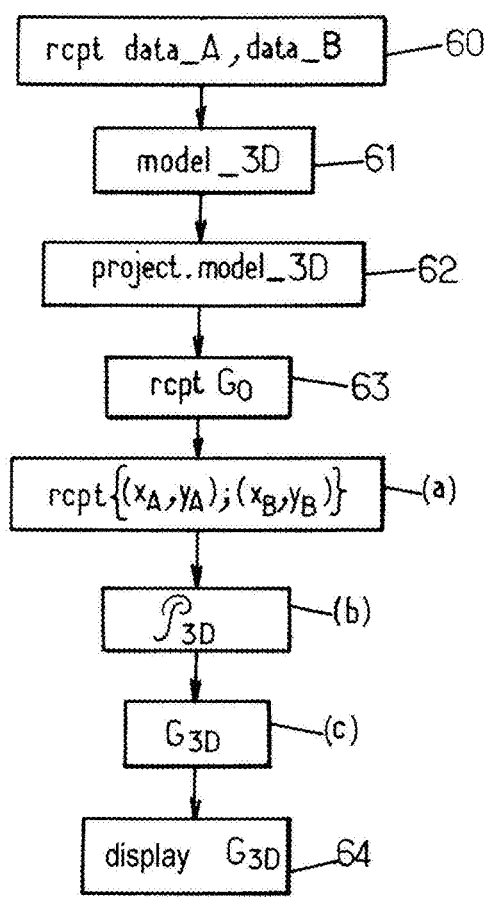
FIG. 6 shows an example of an algorithm of a method according to one embodiment of the invention.

FIG. 6 shows another algorithm, in which two sets of imaging data are received during a step 60. Two stereoscopic images obtained from these sets are displayed. The practitioner may mark certain particular points on one and on the other of the images. A 3D model is reconstructed based on these images, on an a priori model of the structure to be reconstructed, and of the particular points paired from one image to the other (step 61).

Then the obtained model is projected onto two non-parallel planes, for example defined by the practitioner, during a step 62.

The practitioner may then wish to take measurements of geometric quantities intrinsic to the osteo-articular system of the patient. The practitioner clicks on one of the icons 25 to 29, so that an indication of the type of quantity that it is desired to measure is received during a step 62. Registration data are received during a step (a), geometric primitives $P_{3D}$ are determined during a step (b) and a quantity $G_{3D}$ is computed based on these primitives $P_{3D}$, during a step (c). This quantity $G_{3D}$ is displayed on a screen during a step 64.

The invention claimed is:
1. Method for measuring geometric quantities intrinsic to an anatomical system, based on two geometrically calibrated, stereoscopic, two-dimensional images of the anatomical system of a patient, comprising

(a) receiving registration data comprising at least one set of two-dimensional coordinates, each set of two-dimensional coordinates comprising
- a first pair of two-dimensional coordinates corresponding to a first point on one of the said two stereoscopic images and
- a second pair of two-dimensional coordinates corresponding to a second point on the other of the said two stereoscopic images, (b) by using geometric calibration information, determining at least one three-dimensional geometric primitive defined by at least one portion of the registration data received in step (a), (c) computing, based on at least one three-dimensional geometric primitive determined in step (b), a value of geometric quantity intrinsic to the anatomical system, at least one value of geometric quantity being computed in at least one plane defined relative to the osteo-articular system of the patient, based on at least one projection on the said at least one plane of at least one three-dimensional geometric primitive determined in step (b), the said plane being defined based on registration data received in step (a).

2. Measurement method according to claim 1, in which the two stereoscopic images are obtained by two respective projections of a three-dimensional model of the osteo-articular system of the patient in distinct directions on virtual planes simulating acquisition planes.

3. Measurement method according to claim 1, in which the two stereoscopic images are received from two respective X-ray detectors.

4. Measurement method according to claim 1, in which, in step (a), the registration data are received following the selection, by a user, of points on the images with the aid of a user interface.

5. Measurement method according to claim 1, also comprising a step of displaying on a screen the value of geometric quantity computed in step (c).

6. Measurement method according to claim 5, in which, following the display step, the steps (a), (b), (c) and the display step are repeated.

7. Measurement method according to claim 1, in which the registration data received in step (a) comprise three or four sets of two-dimensional coordinates.

8. Measurement method according to claim 7, in which the geometric quantity the value of which is computed in step (c) is an angle.

9. A non-transitory computer-readable recording medium storing therein a computer program for causing a computer to perform the method according to claim 1.

10. Device for measuring geometric quantities intrinsic to an anatomical system, based on two geometrically calibrated, stereoscopic, two-dimensional images of the anatomical system of a patient, comprising
(a) means for receiving registration data comprising at least one set of two-dimensional coordinates, each set of two-dimensional coordinates comprising a first pair of two-dimensional coordinates corresponding to a first point on one of the said two stereoscopic images and a second pair of two-dimensional coordinates corresponding to a second point on the other of the said two stereoscopic images,
(b) processing means for, by using the geometric calibration information, determining at least one three-dimensional geometric primitive defined by at least one portion of the registration data received by the reception means, and for computing, based on at least one three-dimensional geometric primitive thus determined, a value of geometric quantity intrinsic to the anatomical system, wherein at least one value of geometric quantity is computed in at least one plane defined relative to the osteo-articular system of the patient, based on at least one projection on the said at least one plane of at least one three-dimensional geometric primitive thus determined, the said plane being defined based on registration data received by the reception means.

* * * * *